United States Patent
Giustetto et al.

(10) Patent No.: US 12,397,056 B2
(45) Date of Patent: *Aug. 26, 2025

(54) SYSTEM FOR INDUCING SONOPORATION OF A DRUG INTO CANCER CELLS AND METHOD THEREOF

(71) Applicants: Freedom Waves S.R.L, Reggio Emilia (IT); Pierangela Giustetto, Turin (IT)

(72) Inventors: Pierangela Giustetto, Turin (IT); Daniele Faletto, Reggio Emilia (IT)

(73) Assignee: Freedom Waves S.R.L. (IT)

(*) Notice: Subject to any disclaimer, the term of this patent is extended or adjusted under 35 U.S.C. 154(b) by 0 days.

This patent is subject to a terminal disclaimer.

(21) Appl. No.: 18/308,247

(22) Filed: Apr. 27, 2023

(65) Prior Publication Data
US 2024/0382595 A1  Nov. 21, 2024

Related U.S. Application Data

(62) Division of application No. 16/955,457, filed as application No. PCT/IB2018/060508 on Dec. 21, 2018, now Pat. No. 11,648,312.

(51) Int. Cl.
*A61K 41/00* (2020.01)
*A61K 31/337* (2006.01)
(Continued)

(52) U.S. Cl.
CPC ........ *A61K 41/0047* (2013.01); *A61K 31/337* (2013.01); *A61K 31/4745* (2013.01);
(Continued)

(58) Field of Classification Search
CPC .............. A61K 41/0047; A61K 31/337; A61K 31/4745; A61K 31/513; A61K 31/704;
(Continued)

(56) References Cited

U.S. PATENT DOCUMENTS 7,713,200 B1 *  5/2010  Sarvazyan ............. A61B 5/417
                                                          600/447
2009/0281464 A1 * 11/2009  Cioanta .................. A61B 90/96
                                                          601/2
(Continued)

FOREIGN PATENT DOCUMENTS

EP            1774989 A2 *  4/2007  ........... A61B 8/4438
WO    WO-2006127953 A2 * 11/2006  ......... A61K 41/0028
(Continued)

OTHER PUBLICATIONS

Liu et al. "High intensity focused ultrasound-induced gene activation in solid tumors", The Journal of the Acoustical Society of America 120, 492 (2006); doi: 10.1121/1.2205129 (Year: 2016).*
(Continued)

*Primary Examiner* — Joshua B Blanchette
(74) *Attorney, Agent, or Firm* — Widerman Malek, PL; Mark Malek; Jonathan Staudt

(57) ABSTRACT

A method for controlling ultrasonic waves to induced sonoporation of a drug into cancer cells in a tumor. The method may include accessing configuration data that may include a type of the tumor and a type of drug, and determining values of operational parameters that may be based on the configuration data to define determined values. The operational parameters may include frequency value and duty cycle value. The method may also include determining frequency value which may be based on the type of tumor that may define a determined frequency value, and determining the duty cycle value which may be based on the type of drug and the type of tumor that may define a determined duty cycle value.

20 Claims, 10 Drawing Sheets

(51) Int. Cl.

| | | |
|---|---|---|
| *A61K 31/4745* | (2006.01) | |
| *A61K 31/513* | (2006.01) | |
| *A61K 31/704* | (2006.01) | |
| *A61N 7/00* | (2006.01) | |
| *A61P 35/00* | (2006.01) | |
| *B06B 1/02* | (2006.01) | |
| *G16H 20/17* | (2018.01) | |
| *G16H 40/40* | (2018.01) | |
| *G16H 40/67* | (2018.01) | |
| *G16H 50/50* | (2018.01) | |
| *G16H 50/70* | (2018.01) | |
| *G16H 70/40* | (2018.01) | |
| *G16H 70/60* | (2018.01) | |

(52) U.S. Cl.
CPC .......... *A61K 31/513* (2013.01); *A61K 31/704* (2013.01); *A61N 7/00* (2013.01); *A61P 35/00* (2018.01); *B06B 1/0215* (2013.01); *G16H 20/17* (2018.01); *G16H 40/40* (2018.01); *G16H 40/67* (2018.01); *G16H 50/50* (2018.01); *G16H 50/70* (2018.01); *G16H 70/40* (2018.01); *G16H 70/60* (2018.01); *A61N 2007/0004* (2013.01); *A61N 2007/0078* (2013.01); *B06B 2201/55* (2013.01); *B06B 2201/76* (2013.01)

(58) Field of Classification Search
CPC .............. A61N 7/00; A61N 2007/0004; A61N 2007/0078; A61P 35/00; B06B 1/0215; B06B 2201/55; B06B 2201/76; B06B 1/02; G16H 20/17; G16H 40/40; G16H 40/67; G16H 50/50; G16H 50/70; G16H 70/40; G16H 70/60; G16H 20/10; G16H 20/30; G16H 40/63; A61M 37/0092

See application file for complete search history.

(56) References Cited

U.S. PATENT DOCUMENTS

2018/0243418 A1* 8/2018 Husseini ............ A61K 47/6889
2018/0296859 A1* 10/2018 Guha ...................... A61P 35/00

FOREIGN PATENT DOCUMENTS

| WO | WO-2010118307 A1 * | 10/2010 | ............... A61N 7/00 |
| WO | WO-2014008594 A1 * | 1/2014 | ......... A61K 41/0028 |
| WO | WO-2016196741 A2 * | 12/2016 | ............. A61B 5/055 |
| WO | WO-2016198859 A1 * | 12/2016 | |

OTHER PUBLICATIONS

Rizzitelli et al., "The release of Doxorubicin from liposomes monitored by MRI and triggered by a combination of US stimuli led to a complete tumor regression in a breast cancer mouse model", Journal of Controlled Release 230 (2016) 57-63 (Year: 2016).*
U.S. Appl. No. 16/955,457, filed Jun. 18, 2020.

* cited by examiner

Closing time: 6 min

Closing time: >8 min

Closing time: >8 min

Closing time: 4 min

SYSTEM FOR INDUCING SONOPORATION OF A DRUG INTO CANCER CELLS AND METHOD THEREOF

RELATED APPLICATIONS

This application is a divisional application of and claims priority under 35 U.S.C. § 120 of U.S. patent application Ser. No. 16/955,457 filed on Jun. 18, 2020 and titled SYSTEM FOR INDUCING SONOPORATION OF A DRUG INTO CANCER CELLS AND METHOD THEREOF, which in turn is a national phase application of and claims priority under 35 U.S.C. § 371 of PCT Application No. PCT/IB2018/060508 filed on Dec. 21, 2018 and titled SYSTEM FOR INDUCING SONOPORATION OF A DRUG INTO CANCER CELLS AND METHOD THEREOF, which in turn is a PCT International Application of and claims priority under PCT Article 8 of Italian Patent Application Serial No. 102017000148858 filed on Dec. 22, 2017 and titled SYSTEM FOR INDUCING SONOPORATION OF A DRUG INTO CANCER CELLS AND METHOD THEREOF. The content of these applications are incorporated herein by reference, except for where the contents therein conflict with the contents herein.

FIELD OF THE INVENTION

The present invention relates to systems and methods for inducing sonoporation of a drug into cancer cells in a tumor for enhancing the uptake of the drug into the target (i.e. the tumor). The invention relates also to a method for controlling ultrasound waves in such a way to induce sonoporation of a drug into cancer cells thus improving the uptake of the drug into the target.

BACKGROUND OF THE INVENTION

After circulatory diseases, cancer is nowadays the second most common cause of death in the world. The International Agency for Research on Cancer has estimated that, due to the ageing of the population, it is expected, in 2030, an increasing of cancer cases of about 21.7 million with a death rate of 13 million of people. The known oncologic therapies are based on chemotherapy and/or radiotherapy and/or surgical removal of tumor mass.

Conventional chemotherapy, in particular, suffers lack of selectivity for cancer cells and, therefore, can give rise to side effects at both systemic and local level. Moreover, the tumors often develop a resistance to the administered chemotherapy drugs. For these reasons, in the last decades, several techniques were developed to improve the selectivity of the drug delivery by using specialized lipid structure, termed a liposome. Liposomes are nanocarriers generically comprising an enclosed lipid droplet having a core, typically an aqueous core, containing the drug (e.g. a chemotherapy agent, an anti-inflammatory drug, a cytotoxic agent, etc).

The liposomes for encapsulating chemotherapy drug, in particular, are usually designed with a structure allowing for a prolonged circulation time in blood of the liposome itself and, therefore, of the drug contained in the liposome. Prolonged longevity in blood allows longer interaction of liposomes with the target (i.e. the tumor) because the higher number of passages of blood through the tumor improves the enhanced permeability and retention (EPR) effect. Thus, the global uptake of the drug into the tumor is enhanced and marked improvements of the therapeutic index of the transported drug is yielded [Deshpande P. P., Biswas S., and V. P Torchilin V. P., "Current trends in the use of liposomes for tumor targeting" Nanomedicine 2013 September; 8 (9)], [Torchilin V. P. "Targeted pharmaceutical nanocarriers for cancer therapy and imaging". 5 AAPS J. 2007; 9 (2): 128-147].

However, even if liposomal formulation of chemotherapy drugs is used, the selectivity level and the therapeutic efficacy obtained by means of spontaneous release following the natural degradation of the liposome is not yet fully satisfying. For these reasons, even if the nanomedicines currently approved for clinical use release the drug spontaneously, several techniques has been experimentally tested for triggering such release by means of externally-applied stimuli. It has been well established that the improvement in the control of the drug release can be achieved using high intensity focused ultrasound that beside stimulating drug release by means of a local increasing of the temperature, cause cytotoxic effects by itself and induce coagulative necrosis of the tumor and of the surrounding tissue (EP 1774989 B1). Shock waves were also used to perform medical treatments aimed to pushed substances inside the human body, tissues or cells and therefore for provisioning of vaccines, anesthetic agents, antibiotics etc (US2009/281464 A1).

For avoiding possible toxic side effects associated with local heating and with the spread of cancerous material following the necrosis of the tumor cells, more recently, pulsed low intensity non-focused ultrasounds (pLINFUs) were employed. pLINFUs are able to perform "insonation" of the liposomes and "sonoporation" of the cell membranes. The term "insonation" refers, in particular, to the induction of the drug release from inside to the outside the liposomes. The term "sonoporation" refers, instead, to the creation of transient non-lethal perforations in cell membranes to aid ingress of liposomes into the cells. It has been demonstrated that, differently from the high intensity focused ultrasound, the lower energy ($<3$ W/cm$^2$) associated with pLINFU produces minimal thermal effects [Rizzitelli S., Giustetto P., Faletto D., Delli Castelli D., Aime S., Terreno E. "The release of Doxorubicin from liposomes monitored by MRI and triggered by a combination of US stimuli led to a complete tumor regression in a breast cancer mouse model.", J Control Release, 2016; 230:57-63.].

The pLINFUs, if compared with the pulsed low intensity focused ultrasounds, or PLIFUs, like those employed in the method and system described in WO2016/196741, are characterized by different ultrasonic distribution field at the same frequency, piezoelectric diameter and number of excitation cycles. The pLINFUs has a more regular geometric distribution 5 than the pLIFUs due to the flat geometry of the piezoelectric transducer generating the pLINFUs. Such flat geometry, in addition, allows for sonoporating a larger volume than the volume sonoporable by pLIFUs that are, instead, generated by the convergence of the ultrasonic beams from two or more piezoelectric transducers. Moreover, in the point of convergence of the at least two ultrasonic beams, interference phenomena can occur with no possibility to estimate the consequent distortion caused by those. Prior art pLIFU systems adopt methods to reduce this phenomenon, but the inhomogeneity of the medium or of the biological tissues crossed by the ultrasounds, can cause other unpredictable interferences.

For these reasons only with pLINFUs, it is possible to guarantee that the ultrasounds waves used for sonoporation reach the target cells with the set frequency and set duty cycle. The sonoporation, indeed, generates biophysical phenomena at the nanometer scale only with specific frequency and duty cycle values that are dependent on the type of cells to be sonoporated and the type of drugs to be entered into the membranes of such cells. Pulsed ultrasound, indeed, consists of an alternation of emission periods (ON periods), and silence periods (OFF periods). The OFF period interrupts the emission period and alternates with the ON periods.

More particularly, the ON period should be dependent on the characteristic of the vector containing the drug and the characteristics of cell membranes; the vibration deriving from the resonance effect of the vector interacts with the cell membrane favoring the opening of the pores and protecting the cell from the direct effects of ultrasound. The duration of the OFF period is determined as a function of the opening and closing characteristic of cellular pores. The OFF period has the function of not further stimulating the cell membrane once the pores have been opened up, facilitating the entry of the vector into the cellular compartment while the same pores are closing. If an ON period is adopted for an extended period of time without an OFF period, the result would be a continuous and prolonged stress of the cell membrane, which in addition to interfering with the correct intracellular 5 accumulation of the drug could provoke excessive stress levels on the cells and in and out phenomena, which causes at the same time the entry and exit of the drug.

Furthermore a prolonged stimulation can cause cell death, which would have as a result the leakage of the cytoplasmic contents (including the drug) with the risk that it can be conveyed to other unwanted sites through the blood flow. For the reasons detailed above, only ultrasound beams having specific values of frequency and duty cycle, are able to interact with the membranes at the lattice level by generating a vibrational pulse or phonon. The latter, propagating through the lattice points thanks to the comparable value of the frequencies of the phononic pulse and of the frequencies of movement of the membrane phospholipids, causes the dislocation of the membrane components and thus triggers the phenomenon of transient pore opening of the membrane.

If non-focused beam (i.e. pLINFUs) are employed, there is no constructive or destructive interference between the ultrasounds that make up the emission beam; this ensures that all the component beams can respect the pulses established according to all the tissue characteristics that are to be treated and the drugs used. The propagation of the phononic pulse and thus the triggering of the transient opening of the membrane pores is influenced also by the acoustic streaming effect. The latter is defined as a small scale eddying of fluid near a vibrating structure such as cell membranes; this phenomenon is known to affect diffusion rates and membrane permeability and, more particularly, to cause a decrease in the useful path, i.e. the path that the ultrasonic beam can travel without interacting with a tissue deformed by the sound pressure itself. [Nowicki A., Kowalewski T., Secomski W., Wo'jcik J., "Estimation of acoustical streaming: theoretical model, Doppler measurements and optical visualization", European Journal of Ultrasound 1998, 7:73-81].

The acoustic streaming effect is different if pLIFUs or if pLINFUs are applied. In the case of pLIFUs, in addition to the reduction of the useful path, a distortion of the signal back from the tissue to the piezoelectric transducer can occur. Such distortion is not specific and characteristic of the tissue to be sonoporated and, therefore, it is a further source of uncertainty in the prediction of the frequency and duty cycle of the ultrasound beam the reach the target cells. For this reason it is even more difficult to guarantee that the ultrasounds waves used for sonoporation reach the target cells with the frequency and duty cycle values that are set as optimum for the best interaction with the membranes.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

The object of the present invention is to provide a system that allows to improve the selectivity of the drug and the intake of the same into cancer cells. This is achieved by the system of the present invention by administering pLINFUs for inducing cell sonoporation through generation of the phonon vibration. A further object of the present invention is to provide a method for controlling ultrasound waves for inducing sonoporation of a drug into cancer cells.

As demonstrated in the examples below, the cell death percentage achieved by sonoporation treatment is dependent on the combination of the type of drug used and of the type of tumor threated. More particularly, the results of experimental tests in vitro on human cancer cells listed below, showed that, in order to achieve an important cell death percentage, the duty cycle of pLINFUs should be modulated according the type of drug and cancer cells. The temporal duration of the administration, i.e. the operation time, of pLINFUs, is also important to guarantee the correct timing of opening and closure of the cell membrane pores.

Based on these results, the present invention provides a system and relative method for controlling frequency and duty cycle of pLINFUs inducing sonoporation according configuration data entered by an operator, said configuration data comprising at least the type of tumor and the type of drug. For the purposes of the present description, the wording "low intensity ultrasound" is designating ultrasound waves with a power density lower than 3 W/cm2 and the wording "type of tumor" is designating a denomination indicating the histological type and the organ where the tumor is located. Non-limiting examples of "type of tumor" are therefore "human breast ductal carcinoma", "human pancreatic adenocarcinoma", "estrogen independent human breast adenocarcinoma", "human mucosal melanoma", "human nodular melanoma", "hepatocellular carcinoma", etc. In addition, it is stated that for the purposes of the present description, with the word "drug" it is intended to designate any substance (other than food that provides nutritional support) that, when inhaled, injected, smoked, consumed, absorbed via a patch on the skin, or dissolved under the tongue, causes a temporary physiological (and/or psychological) change in the body and any substance that can be used to enhance contrast and visibility of tissues and/or structures in medical imaging (i.e. contrast medium).

It is clear that, for the purposes of the present invention the term "drug" is used not only to refer to a single substance or agent but also to a solution, composition or mixture of two or more substances or agents. Although the preferred embodiment of the present invention is a system for inducing sonoporation of chemotherapic liposomes into cancer cells, it is remarked here, that the same system can be used also or on chemotherapic drugs not encapsulated in liposomes and, for any cytotoxic agent (i.e agent able to kill the target cell) or cytostatic agent (i.e. agent having the ability to suppress the growth or cell division of the target cell). Moreover, the system of the present invention can be used for sonoporation of any medicaments other than chemotherapic ones (e.g. anti-inflammatory medicament) and for any pathologies other than tumoral ones. In the latter case, the wording "type of tumor" can be replaced by the wording "type of pathology" indicating the histological type and the organ affected by the pathology.

The above mentioned objects are achieved by the present invention by providing a system comprising a generator configured to provide electrical energy at an ultrasound frequency, at least one ultrasound probe electrically connected to the generator and configured to convert the electrical energy into low intensity non-focalized pulsed ultrasonic waves defined by operation parameters, said operation parameters comprising the frequency and the duty cycle of the ultrasonic waves; characterized in that the system further comprises: an input device enabling an operator to enter configuration data comprising: type of tumor and type of drug; and a processor configured to: determine the values of said operation parameters on the basis of the entered configuration data, wherein the value of the frequency is determined on the basis of at least the type of tumor, and the value of the duty cycle is determined on the basis of at least the type of drug and the type of tumor; and control the generator and the ultrasound probe to operate according to said determined values.

More particularly, the determination of the values of the operation parameters on the basis of the entered configuration data, is performed by the processor through the following steps: assigning a value of frequency to a type of tumor; and assigning a value of duty cycle to a couple of configuration data comprising: a type of tumor and a type of drug.

To this aim the system comprises a computer readable memory storing a list of values of frequency and a list of values of duty cycle. In the system of the present invention the type of drug is, preferably, selected from the group consisting of: paclitaxel, paclitaxel albumine, doxorubicin, liposomal doxorubicin, irinotecan and liposomal irinotecan and fluoruracil and the determined value of the duty cycle is, preferably, below 12%.

The aforementioned object is also achieved by the present invention by providing a method comprising: reading configuration data entered by an operator, said configuration data comprising: type of tumor, type of drug, grade of tumor, and anthropometric measurements; determining the values of operation parameters of the ultrasound waves on the basis of at least the type of tumor and the type of drug, said parameters comprising frequency and duty cycle; controlling at least one ultrasound probe to operate according to said determined values, said at least one probe being electrically connected to a generator and configured to convert the electrical energy into ultrasonic waves; the operation of reading, determining and controlling being performed by means of a processor.

The present invention relates also to a computer program comprising code portions adapted to perform the method detailed above, and a computer readable medium storing computer program code for performing such a method, when run on a computer. Although the value of frequency should be determined at least on the basis of the type of tumor, it has been considered that for those types of tumor, which are not superficial and are localized in particular body regions (e.g. abdomen), also other configuration data have to be accounted for. It is known, indeed, that the depth of penetration of ultrasound waves is influenced by the ultrasound frequency and that the depth of penetration is greater with lower frequencies.

In soft tissues, for example, the average depth of penetration (i.e the depth at which the ultrasound intensity is 20 reduced of 50% with respect to the initial intensity) is 4-5 cm if the ultrasound frequency is 1 MHz and about 1.5 cm if the frequency is 3 MHz. The maximum depth of penetration in soft tissues is, instead, 10-12 cm if the ultrasound frequency is 1 MHz and 3-4 cm is the ultrasound frequency is 3 MHz. With reference to the present invention, the dependence of the depth of penetration on the frequency is implicitly considered by stating the frequency is dependent on the type of tumor. Indeed, if the type of tumor is, for example, one of the melanomas, the tumor is on the body surface, whereas if the type of tumor is breast ductal carcinoma, the tumor is at a certain depth under the body surface. For these reasons, stating that the frequency is determined considering the type of tumor, means, in general, that the frequency is determined also considering the information regarding the depth of the tumor under the body surface.

However, there are some type of tumor (e.g. pancreatic adenocarcinoma) that are located in body districts whose dimensions can strongly varied among individuals. In these cases, the inter-individual body differences (e.g. abdominal circumference) can significantly affect the determination of the frequency necessary to guarantee that ultrasounds reach the tumor. As a consequence, the value of ultrasound frequency should be also determined on the basis of anthropometric measurements of the patient. More particularly, for human pancreatic adenocarcinoma, some examples of such anthropometric measurement can be: abdominal circumference, body mass index and body fat percentage.

For human breast ductal carcinoma and estrogen independent human breast adenocarcinoma, some examples of such anthropometric measurement can be: breast circumference, body mass index, body fat percentage, thorax circumference. Hence, in the system of the present invention, the configuration data can further comprise anthropometric measurements of the patient to which the cancer cells belongs, said anthropometric measurements being selected from the group consisting of: abdominal circumference, body mass index, breast circumference, thorax circumference, and body fat percentage and the value of the frequency can be determined also on the basis of the anthropometric measurements. In the system of the present invention, the determined value of the frequency is comprised between 0.6 MHz and 3 MH.

Although the value of duty cycle should be determined at least on the basis of the type of tumor and of the type of drug, it has been considered that when a tumor is a metastasis, or secondary tumor, its localization can be different from that indicated in the "type of tumor" denomination and the cells are thus different from the cells of the corresponding primitive tumor, because they belongs to an organ which is different from that in which the tumor originated. Since the duty cycle, as detailed in the examples below, has to be varied according the type of cells in which it is desired to induce sonoporation, the duty cycle has to be varied according the localization of an eventual secondary tumor. For these reasons, in the system of the present invention the configuration data can further comprise the grade of the tumor and, if it is a metastasis, the localization of the said metastasis.

A further operation parameter that is relevant for obtaining an effective sonoporation of the drug into cancer cells is the operation time, i.e. the temporal interval of the administration of the ultrasounds. As explained in details in the examples below, the value of the operation time is also relevant in order to guarantee an effective sonoporation of the drug into cells. For this reason in the system of the present invention the operation parameters can comprise the operation time, the value of said operation time being determined on the basis of at least the type of tumor and the type of drug.

The system of the present invention is further configured to automatically tune the frequency and the amplitude of the ultrasound probe to compensate the attenuation of the ultrasound waves caused by any medium interposed between the probe and the cancer cells. Moreover, the automatically tuning of the frequency and the amplitude occurs synchronously with the duty cycle. These and other features will be made clearer with the aid of the following detailed description of a preferred embodiment of the invention, to be read by way of non-limiting example of the more general principle claimed.

With the foregoing in mind, embodiments of the present invention are related to a method for controlling ultrasonic waves to induced sonoporation of a drug into cancer cells in a tumor. The method may include accessing configuration data that may include a type of the tumor and a type of drug, and determining values of operational parameters that may be based on the configuration data to define determined values. The operational parameters may include frequency value and duty cycle value. The method may also include determining frequency value which may be based on the type of tumor that may define a determined frequency value, and determining the duty cycle value which may be based on the type of drug and the type of tumor that may define a determined duty cycle value.

Some embodiments of the present invention may include automatically tuning the determined frequency value and an amplitude of the ultrasonic waves to compensate for attenuation of the ultrasonic waves caused by a medium interposed between at least one ultrasound probe used to emit the ultrasonic waves and the cancer cells. The determined frequency value and the amplitude of the ultrasonic waves may be automatically tuned synchronously with the duty cycle value. The at least one ultrasound probe may include a plurality of ultrasound transducers.

The plurality of ultrasound transducers may include a first subset of ultrasound transducers and a second subset of ultrasound transducers. The first subset of ultrasound transducers may be configured as ultrasound emitters which may convert electrical energy into the ultrasonic waves for inducing sonoporation. The second subset of ultrasound transducers may be configured as ultrasound receivers that may convert ultrasonic waves reflected by the medium interposed into an electric signal readable by a processor.

Some embodiments of the present invention may also include calculating a difference of frequency and amplitude between the ultrasonic waves emitted by the first subset of transducers and the ultrasonic waves received by the second subset of transducers, which may define calculated differences. Some embodiments may also include adjusting the amplitude and the frequency of the ultrasonic waves to compensate for the calculated differences.

The at least one ultrasound probe may comprise an ultrasound transducer. The ultrasound transducer may be configured as an ultrasound emitter that may convert electrical energy into the ultrasonic waves for inducing sonoporation. The ultrasound transducer may be further configured as an ultrasound receiver that may convert the ultrasonic waves reflected by the medium interposed into an electric signal readable by a processor. Some embodiments of the present invention may include calculating a difference of frequency and amplitude between the ultrasonic waves emitted and the ultrasonic waves received by the ultrasound transducer, which may define a calculated difference, and adjusting the amplitude and the frequency of the ultrasonic waves to compensate for the calculated difference.

Embodiments of the prevent invention may further include storing a list of values of frequency and a list of values of duty cycle on a computer readable memory, assigning a value of frequency to a type of tumor, defining a coupled configuration data that includes a type of tumor and a type of drug, and assigning a value of duty cycle to the coupled configuration data. The tumor may comprise human breast ductal carcinoma, estrogen independent human breast adenocarcinoma, human pancreatic adenocarcinoma, human melanoma, human lentiginous melanoma, human lentigo maligna melanoma, human superficial spreading melanoma, human acral lentiginous melanoma, human mucosal melanoma, human nodular melanoma, human polypoid melanoma, human small cell melanoma, human Spitzoid melanoma, human uveal melanoma and human desmoplastic melanoma, hepatocellular carcinoma.

The configuration data may include anthropometric measurements. The anthropometric measurements may include abdominal circumference, body mass index, breast circumference, thorax circumference, and/or body fat percentage. The frequency value of the operational parameter may be determinable based on the anthropometric measurements. Some embodiments of the present invention may include defining a set of coupled configuration data that may include a type of tumor and one or more anthropometric measurements, and assigning a value of the frequency to the set of coupled configuration data.

The configuration data may also include a grade of the tumor. The grade of the tumor may comprise primary tumor, primitive tumor, and secondary tumor, and/or metastasis. The configuration data may further include a localization of a secondary tumor. The duty cycle value may be determinable based on the localization of the secondary tumor. Some embodiments of the present invention may further include defining a set of coupled configuration data which may include the type of tumor, the type of drug, the grade of the tumor, and/or the localization of the secondary tumor. Some embodiments may also include assigning a value of the duty cycle to the set of coupled configuration data.

The type of drug may include paclitaxel, paclitaxel albumine, doxorubicin, liposomal doxorubicin, irinotecan, liposomal irinotecan and/or fluorouracil. The operational parameters may comprise an operation time of the ultrasonic waves. A value of the operation time may be determinable based on the type of tumor and/or the type of drug. Some embodiments may include defining a coupled configuration data which may include the type of tumor and/or the type of drug, and assigning the value of the operation time to the coupled configuration data.

In some embodiments of the present invention the operation time may comprise a single temporal window in which ultrasonic waves are administered, and/or at least two temporal windows in which during a first one of the at least two temporal windows, ultrasonic waves may be administered. During a second one of the at least two temporal windows, no ultrasonic waves may be administered, so that ultrasonic waves may be administered in alternating temporal windows and may be separated by a single temporal window where no ultrasonic waves may be administered. The determined frequency value may be between 0.6 MHz and 3 MHZ, and the determined duty cycle value may be below 12%.

Some embodiments of the present invention may comprise a computer program product that may include code to control ultrasonic waves to induced sonoporation of a drug into cancer cells in a tumor. The computer program product may be operable to access configuration data that may include a type of the tumor and/or a type of the drug. The computer program product may be operable to determine values of operational parameters which may be based on the configuration data to define determined values. The operational parameters may include frequency value and/or duty cycle value. The computer program product may also be operable to determine frequency value and/or determine duty cycle value. Frequency value may be determined based on the type of tumor to define a determined frequency value. The duty cycle value may be determined based on the type of drug and/or the type of tumor to define a determined duty cycle value.

Some embodiments of the present invention may comprise a computer readable medium to store a computer program code that may control ultrasonic waves to induced sonoporation of a drug into cancer cells in a tumor. The computer program product may be executable to access configuration data that may include a type of the tumor and/or a type of the drug. The computer readable medium may be executable to determine values of operational parameters which may be based on the configuration data to define determined values. The operational parameters may include frequency value and/or duty cycle value. The computer readable medium may also be executable to determine frequency value and/or determine duty cycle value. Frequency value may be determined based on the type of tumor to define a determined frequency value. The duty cycle value may be determined based on the type of drug and/or the type of tumor to define a determined duty cycle value.

BRIEF DESCRIPTION OF THE DRAWINGS

Some embodiments of the present invention are illustrated as an example and are not limited by the figures of the accompanying drawings, in which like references may indicate similar elements.

FIG. 7 shows in particular the uptake of FA into human pancreatic adenocarcinoma cells in five experimental conditions, said conditions being specifically designed in order to investigate the effect of the administration of ultrasounds;

DETAILED DESCRIPTION OF THE INVENTION

Figure 1A:
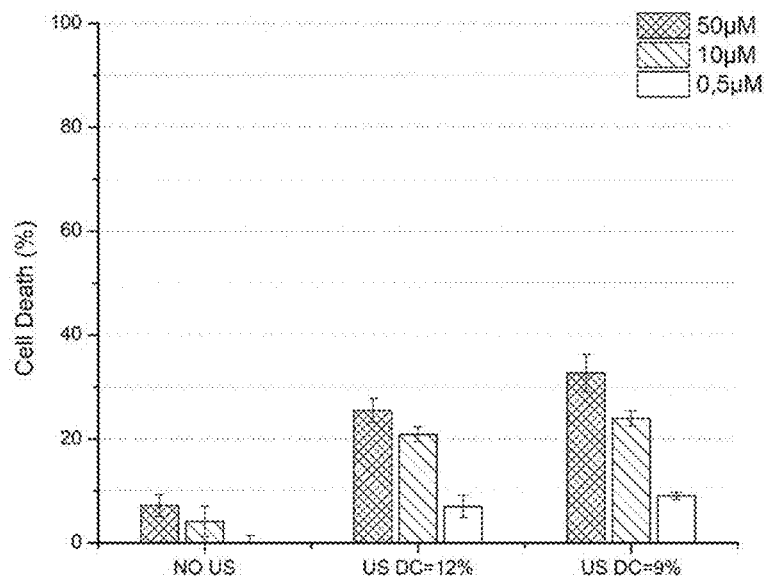
FIG. 1a shows the percentage of cell death obtained by in-vitro administering paclitaxel to human breast ductal carcinoma cells, said administration being performed simultaneously to the administration of ultrasound waves. The figure shows the results obtained with different total concentrations (50 µM, 10 µM, 0.5 µM)

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

A preferred embodiment of the system of the present invention comprises:
a generator configured to provide electrical energy at an ultrasound frequency;
an ultrasound probe electrically connected to the generator and configured to
convert the electrical energy into low intensity non-focalized pulsed ultrasonic waves defined by operation parameters, said operation parameters comprising the frequency, the duty cycle and the operation time of the ultrasonic waves;
an input device enabling an operator to enter configuration data comprising: type of tumor, type of drug, anthropometric measurements of the patient to which cancer cells belongs and grade of the tumor; and
a processor configured to:
determine the values of said operation parameters on the basis of the entered configuration data, wherein the value of the frequency is determined on the basis of the type of tumor and of the anthropometric measurements and the value of the duty cycle is determined on the basis of at least the type of drug and the type of tumor; and
control the generator and the ultrasound probe to operate according to said determined values.

More particularly, the system of the present invention comprises a computer readable memory storing a list of values of frequency and a list of values of duty cycle and the processor is thus configured to:
assign a value of frequency to a type of tumor; and
assign a value of duty cycle to the couple of configuration data comprising: a type of tumor and a type of drug.

The power density of ultrasound waves generated by the preferred embodiment of the system is less than 3 W/cm$^2$. The input device is preferably a touch screen integrated with the system. Other examples of input device are a laptop, a tablet and a smartphone. In the preferred embodiment of the present invention, the first configuration data that the operator is requested to enter, is the type of drug. The type of drug is selected from the group consisting of: paclitaxel, paclitaxel albumine, doxorubicin, liposomal doxorubicin, irinotecan, liposomal irinotecan and fluorouracil.

After selecting from a menu list or entering by typing the type of drug, an operator can be requested to choose the type of tumor. The type of tumor is selected from the group consisting of human breast ductal carcinoma, estrogen independent human breast adenocarcinoma and human pancreatic adenocarcinoma. The grade of tumor has then to be entered by selecting the following two options: primary tumor (i.e. primitive tumor), and secondary tumor (i.e. metastasis). If the selected grade of tumor is:
primary tumor, the duty cycle is determined on the basis of the type of drug and the type of tumor.
secondary tumor, also the localization of the secondary tumor have to be entered by the operator. In this case the duty cycle is determined on the basis of the type of drug, the type of tumor and the localization of the secondary tumor.

In this case, the processor is configured to assign a value of duty cycle to the set of configuration data comprising the type of tumor, the type of drug, the grade of the tumor and, eventually, the localization of the secondary tumor. For example, if the entered grade of tumor is primary, the entered type of tumor is human breast ductal carcinoma or estrogen independent human breast adenocarcinoma and the entered type of drug is paclitaxel or paclitaxel albumin or doxorubicin or liposomal doxorubicin, the assigned duty cycle is 9%.

For example, if the entered grade of tumor is primary, the entered type of tumor is human pancreatic adenocarcinoma and the entered type of drug is paclitaxel or paclitaxel albumin or irinotecan or liposomal irinotecan or fluorouracil, the assigned duty cycle is 1%. After selecting the grade of tumor, anthropometric measurements have to be entered. The anthropometric measurement that have to be specified by the operator are different according to the type of tumor if the grade of tumor is a primary tumor and according to localization of the secondary tumor if the grade of tumor is secondary tumor. For example, anthropometric measurements can comprise abdominal circumference if the type of tumor is human pancreatic adenocarcinoma, and breast circumference if the type of tumor is human breast ductal carcinoma. The frequency is then determined on the basis of such anthropometric measurements.

In this case, the processor is thus configured to assign a value of frequency to the set of configuration data comprising the type of tumor and at least one anthropometric measurement selected from the group consisting of: abdominal circumference, body mass index, breast circumference, thorax circumference, and body fat percentage. If the tumor extends to different depths, the system of the present invention can also comprise two probes operating at different frequencies corresponding to the different depths. After having completed the entering of the aforementioned configuration data, it is given to the operator also the possibility to choose another set of parameters relative to another tumor.

For example, if the first set of configuration data is referred to a primary tumor, it is possible to set also configuration data relative to a methastasis of said primary tumor. The system of the present invention can, indeed, to provide two probes, one first probe for the primary tumor and a second probe for the metastasis. The ultrasounds emitted from the first probe will have a duty cycle dependent on the type of drug and on the type of the primary tumor, whereas the ultrasounds emitted from the second probe will have a duty cycle dependent on the type of drug, on the type of primary tumor, and of the localization of the second tumor. The operation time for each probe will be also determined on the basis of the configuration data entered. More particularly, according to the type of tumor and the type of drug, the operation time can comprise:

- one temporal window in which ultrasounds are administered; or
- two or more temporal windows in which ultrasounds are administered, said windows being interspaced by one temporal window in which no ultrasounds are administered. The operator is asked for accepting this minimum operation time or to enter another configuration data consisting in an integer number that multiplied by the minimum operation time, results in the operation time.

In this case, the processor is configured to assign a value of operation time to the couple of configuration data comprising: a type of tumor and a type of drug. Finally, in a preferred embodiment, of the system of the present invention, the probe can comprise a plurality of ultrasound transducers, a first subset of said transducers being configured as ultrasound emitters for converting the electrical energy into the ultrasonic waves for inducing sonoporation, and a second subset of said transducers being configured as ultrasound receivers for converting ultrasound waves reflected the any medium interposed into an electric signal readable by the processor, the processor being programmed to:

- calculate the differences of frequency and amplitude between the ultrasound waves emitted by the first subset of transducers and the ultrasound waves received by the second subset of transducers; and
- adjust the values of the amplitude and the frequency of the ultrasound emitted, in such a way to compensate said differences.

The first and the second subset of transducers can be also overlap in an only one transducer. In this case, the probe comprises one ultrasound transducer, configured as an ultrasound emitter for converting the electrical energy into the ultrasonic waves for inducing sonoporation and as an ultrasound receiver for converting ultrasound waves reflected the any medium interposed into an electric signal readable by the processor, the processor being programmed to:

- calculate the differences of frequency and amplitude between the ultrasound waves emitted and the ultrasound waves received by said transducer; and
- adjust the values of the amplitude and the frequency of the ultrasound emitted, in such a way to compensate said differences.

EXAMPLES

The system of the present invention was tested in vitro using two cellular lines of human breast cancer and one cellular line of human pancreatic adenocarcinoma. In particular the following cellular lines were employed:

MCF-7: human breast ductal carcinoma;

MDA-MB-231: estrogen independent human breast adenocarcinoma;

MiaPaCa-2: human pancreatic adenocarcinoma.

The following table summarized the tested combinations of cellular lines and type of drug:

| Cellular Lines | Type of tumor | Type of drug |
| --- | --- | --- |
| MCF -7 | Human breast ductal carcinoma | Paclitaxel |
| MCF -7 | Human breast ductal carcinoma | Paclitaxel albumine |
| MCF -7 | Human breast ductal carcinoma | Doxorubicin |
| MCF -7 | Human breast ductal carcinoma | Liposomal Doxorubicin |
| MDA-MB-231 | Estrogen indipendent Human breast adenocarcinoma | Paclitaxel |
| MDA-MB-231 | Estrogen indipendent Human breast adenocarcinoma | Paclitaxel albumine |
| MDA-MB-231 | Estrogen indipendent Human breast adenocarcinoma | Doxorubicin |
| MDA-MB-231 | Estrogen indipendent Human breast adenocarcinoma | Liposomal Doxorubicin |
| MiaPaCa-2 | Human pancreatic adenocarcinoma | Paclitaxel |
| MiaPaCa-2 | Human pancreatic adenocarcinoma | Paclitaxel albumine |

-continued

| Cellular Lines | Type of tumor | Type of drug |
|---|---|---|
| MiaPaCa-2 | Human pancreatic adenocarcinoma | rinotecan |
| MiaPaCa-2 | Human pancreatic adenocarcinoma | Liposomal irinotecan + Fluorouracil |

For each combination the percentage of cell death was measured in three main experimental conditions:
administration of the drug (hereinafter named "NO-US" condition);
administration of the drug and simultaneous administration of non focalized pulsed low-intensity ultrasound with a frequency of 1 MHz and a period of 1 second, said drug being administered in a unique dose;
1 administration of non focalized pulsed low-intensity ultrasound with a frequency of 1 MHz and a period of 1 second, followed by administration of the drug; and
administration of the drug and simultaneous administration of non focalized pulsed low-intensity ultrasound with a frequency of 1 MHz and a period of 1 second, said drug being administered in two doses of equal concentration (hereinafter termed "US-DC" condition).

All the experimental conditions, other than NO-US, were replicated for different values of duty cycle and each experimental condition were replicated for three different total concentrations of drugs. Several operation times were also tested for each cellular lines and for each type of drug. The better results were obtained in US-DC condition by a first administration of a first dose of drug and simultaneous administration of ultrasounds for 20 seconds followed by a second administration of a second dose of drug and simultaneous administration of ultrasound for other 5 seconds.

The results are listed in tables below and showed in the FIGS. 1a, 1b, 2a, 2b, 3a, 3b, 4a, 4b, 5a, 5b, 6a, 6b. The tables in particular summarize the results obtained for the US condition and US-DC condition for the three different total concentration of drugs listed above. For the latter condition two values of duty cycle are chosen to be showed as better representative of the efficacy of the treatment. In particular, for the cellular lines MCF-7 and MDA-MB-231, the results relative to the following values of duty cycle are showed:
duty cycle=12% (US-DC=12%)
duty cycle=9% (US-DC=9%)
For the cellular line MiaPaCa-2, the results relative to the following values of duty cycle are showed:
duty cycle=12% (US-DC=12%)
duty cycle=1% (US-DC=1%).

Example 1

In the following table the percentage of cell death are reported for three different concentration of paclitaxel administered to cells of MCF-7 in three conditions:
NO-US: a first administration of a first dose of paclitaxel without administration of ultrasounds (NO-US) followed by a second administration of a second dose of paclitaxel;
US-DC=12%: first administration of a first dose of paclitaxel and simultaneous administration of pLINFUs (with duty cycle=12%) for 20 seconds followed by a second administration of a second dose of paclitaxel and simultaneous administration of pLINFUs for other 20 seconds;
US-DC=9%: first administration of a first dose of paclitaxel and simultaneous administration of pLINFUs (with duty cycle=9%) for 20 seconds followed by a second administration of a second dose of paclitaxel and simultaneous administration of pLINFUs for other 20 seconds.

| | Paclitaxel - MCF -7 | | | | | |
|---|---|---|---|---|---|---|
| | Cell Death % | Increasing % vs NO-US | Cell Death % | Increasing % vs NO-aUS | Cell Death % | Increasing % vs NO-US |
| | Total concentration 50 µM | | Total concentration 10 µM | | Total concentration 0.5 µM | |
| NO - US | 7.2% | — | 4.1% | — | 1.0% | — |
| US - DC = 12% | 17.8% | +147.3% | 13.2% | +221.6% | 3.4% | +242.5% |
| US - DC = 9% | 32.7% | +354.2% | 24% | +484.7% | 9.1% | +807.5% |

The results of the table above are graphically represented in FIG. 1a.

Example 2

In the following table the percentage of cell death are reported for three different concentration of paclitaxel albumine administered to cells of MCF-7 in three conditions:
NO-US: a first administration of a first dose of paclitaxel albumine without administration of ultrasounds (NO-US) followed by a second administration of a second dose of paclitaxel albumine;
US-DC=12%: first administration of a first dose of paclitaxel albumine and simultaneous administration of pLINFUs (with duty cycle=12%) for 20 seconds followed by a second administration of a second dose of paclitaxel albumin and simultaneous administration of pLINFUs for other 20 seconds;
US-DC=9%: first administration of a first dose of paclitaxel albumine and simultaneous administration of pLINFUs (with duty cycle=9%) for 20 seconds followed by a second administration of a second dose of paclitaxel albumin and simultaneous administration of pLINFUs for other 20 seconds.

| Paclitaxel albumine - MCF -7 | | | | | |
|---|---|---|---|---|---|
| Cell Death % Total concentration 50 µM | Increasing % vs NO-US | Cell Death % Total concentration 10 µM | Increasing % vs NO-US | Cell Death % Total concentration 0.5 µM | Increasing % vs NO-US |
| NO - US | 23.7% | — | 12.9% | — | 2.6% | — |
| US - DC = 12% | 39.9% | +68.3% | 26.5% | +106% | 25.24% | +491.3% |
| US - DC = 9% | 51.7% | +118.1% | 33.7% | +161.8% | 24% | +830% |

Figure 1B:
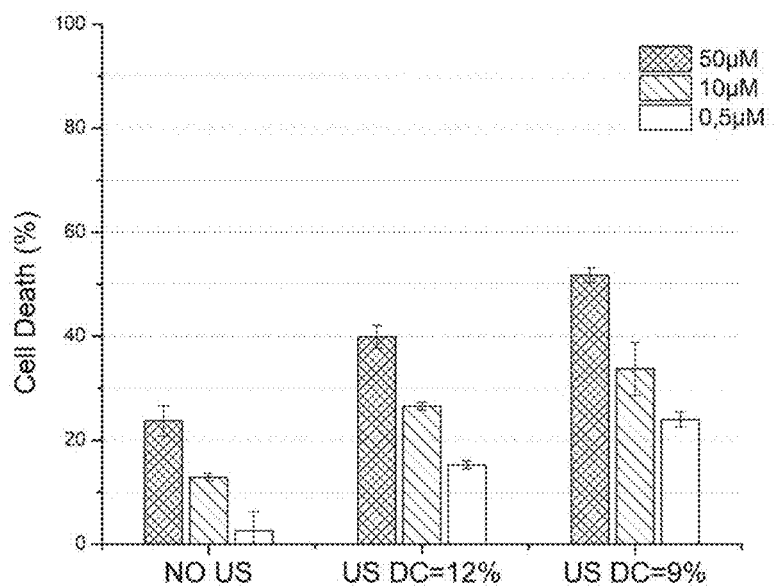
FIG. 1b shows the percentage of cell death obtained by in-vitro administering paclitaxel albumine to human breast ductal carcinoma cells, said administration being performed simultaneously to the administration of ultrasound waves. The figure shows the results obtained with different total concentrations (50 µM, 10 µM, 0.5 µM)

The results of the table above are graphically represented in FIG. 1b.

Example 3

In the following table the percentage of cell death are reported for three different concentration of doxorubicin administered to cells of MCF-7 in three conditions:

NO-US: a first administration of a first dose of doxorubicin without administration of ultrasounds (NO-US) followed by a second administration of a second dose of doxorubicin;

US-DC=12%: first administration of a first dose of doxorubicin and simultaneous administration of pLINFUs (with duty cycle=12%) for 20 seconds followed by a second administration of a second dose of doxorubicin and simultaneous administration of pLINFUs for other 20 seconds;

US-DC=9%: first administration of a first dose of doxorubicin and simultaneous administration of pLINFUs (with duty cycle=9%) for 20 seconds followed by a second administration of a second dose of doxorubicin and simultaneous administration of pLINFUs for other 20 seconds.

| Doxorubicin - MCF -7 | | | | | |
|---|---|---|---|---|---|
| Cell Death % Total concentration 1000 µg/ml | Increasing % vs NO-US | Cell Death % Total concentration 500 µg/ml | Increasing % vs NO-US | Cell Death % Total concentration 100 µg/ml | Increasing % vs NO-US |
| NO - US | 59% | — | 23.3% | — | 17.1% | — |
| US - DC = 12% | 82% | +39% | 49.9% | +114.2% | 28.2% | +64.9% |
| US - DC = 9% | 70.6% | +19.7% | 47.2% | +102.5% | 29.8% | +74.4% |

Figure 2A:
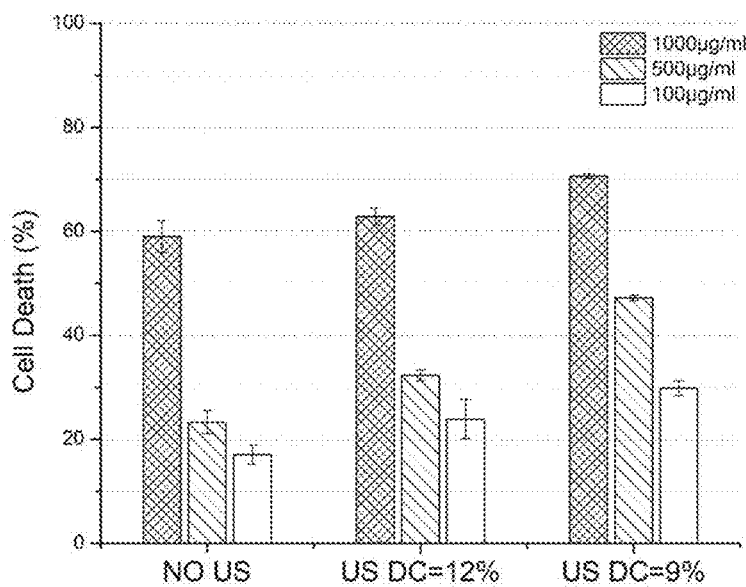
FIG. 2a shows the percentage of cell death obtained by in-vitro administering doxorubicin to human breast ductal carcinoma cells, said administration being performed simultaneously to the administration of ultrasound waves. The figure shows the results obtained with different total concentrations (1000 µg/ml, 500 µg/ml, 100 µg/ml)

The results of the table above are graphically represented in FIG. 2a.

Example 4

In the following table the percentage of cell death are reported for three different concentration of liposomal doxorubicin administered to cells of MCF-7 in three conditions:

NO-US: a first administration of a first dose of liposomal doxorubicin without administration of ultrasounds (NO-US) followed by a second administration of a second dose of liposomal doxorubicin;

US-DC=12%: first administration of a first dose of liposomal doxorubicin and simultaneous administration of pLINFUs (with duty cycle=12%) for 20 seconds followed by a second administration of a second dose of liposomal doxorubicin and simultaneous administration of pLINFUs for other 20 seconds;

US-DC=9%: first administration of a first dose of liposomal doxorubicin and simultaneous administration of pLINFUs (with duty cycle=9%) for 20 seconds followed by a second administration of a second dose of liposomal doxorubicin and simultaneous administration of pLINFUs for other 20 seconds.

| Liposomal doxorubicin - MCF-7 | | | | | |
|---|---|---|---|---|---|
| Cell Death % Total concentration 1000 µg/ml | Increasing % vs NO-US | Cell Death % Total concentration 500 µg/ml | Increasing % vs NO-US | Cell Death % Total concentration 100 µg/ml | Increasing % vs NO-US |
| NO - US  75.4% | — | 35.5% | — | 16.2% | — |
| US - DC = 12%  82% | +8.7% | 49.8% | +40.4% | 28.2% | +74% |
| US - DC = 9%  92.8% | +23% | 47.2% | +97.4% | 37% | +128.7% |

Figure 2B:
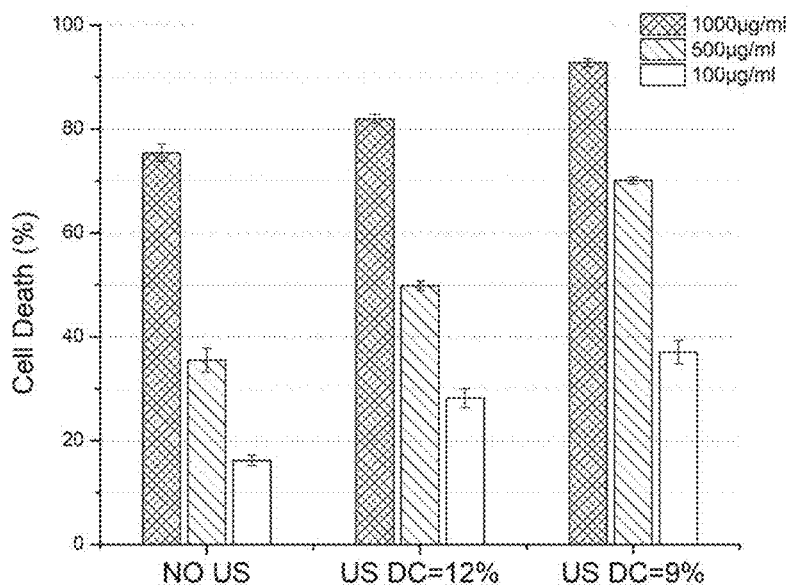
FIG. 2b shows the percentage of cell death obtained by in-vitro administering liposomal doxorubicin to human breast ductal carcinoma cells, said administration being performed simultaneously to the administration of ultrasound waves. The figure shows the results obtained with different total concentrations (1000 µg/ml, 500 µg/ml, 100 µg/ml)

The results of the table above are graphically represented in FIG. 2b.

Example 5

In the following table the percentage of cell death are reported for three different concentration of paclitaxel administered to cells of MDA-MB-231 in three conditions:

NO-US: a first administration of a first dose of paclitaxel without administration of ultrasounds (NO-US) followed by a second administration of a second dose of paclitaxel;

US-DC=12%: first administration of a first dose of paclitaxel and simultaneous administration of pLINFUs (with duty cycle=12%) for 20 seconds followed by a second administration of a second dose of paclitaxel and simultaneous administration of pLINFUs for other 20 seconds;

US-DC=9%: first administration of a first dose of paclitaxel and simultaneous administration of pLINFUs (with duty cycle=9%) for 20 seconds followed by a second administration of a second dose of paclitaxel and simultaneous administration of pLINFUs for other 20 seconds.

| Paclitaxel - MDA-MB-231 | | | | | |
|---|---|---|---|---|---|
| Cell Death % Total concentration 50 µM | Increasing % vs NO-US | Cell Death % Total concentration 10 µM | Increasing % vs NO-US | Cell Death % Total concentration 0.5 µM | Increasing % vs NO-US |
| NO - US  7.9% | — | 6.4% | — | 6.4% | — |
| US - DC = 12%  12.3% | +55.3% | 7.4% | +15% | 5.9% | −7.8% |
| US - DC = 9%  25.5% | +221.9% | 14.7% | +128.4% | 11.3% | +76.6% |

Figure 3A:
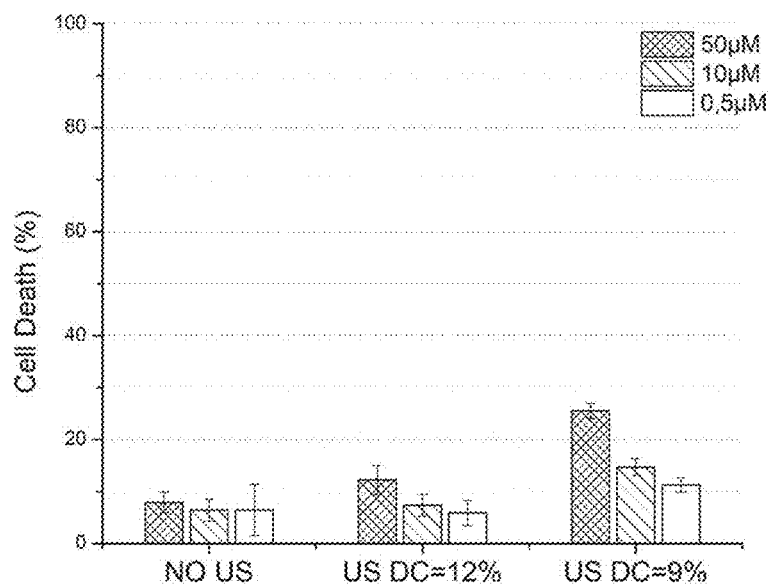
FIG. 3a shows the percentage of cell death obtained by in-vitro administering paclitaxel to estrogen independent human breast adenocarcinoma cells, said administration being performed simultaneously to the administration of ultrasound waves. The figure shows the results obtained with different total concentrations (50 µM, 10 µM, 0.5 µM)

The results of the table above are graphically represented in FIG. 3a.

Example 6

In the following table the percentage of cell death are reported for three different concentration of paclitaxel albumine administered to cells of MDA-MB-231 in three conditions:

NO-US: a first administration of a first dose of paclitaxel without administration of ultrasounds (NO-US) followed by a second administration of a second dose of paclitaxel albumine;

US-DC=12%: first administration of a first dose of paclitaxel albumine and simultaneous administration of pLINFUs (with duty cycle=12%) for 20 seconds followed by a second administration of a second dose of paclitaxel albumin and simultaneous administration of pLINFUs for other 20 seconds;

US-DC=9%: first administration of a first dose of paclitaxel albumine and simultaneous administration of pLINFUs (with duty cycle=9%) for 20 seconds followed by a second administration of a second dose of paclitaxel albumin and simultaneous administration of pLINFUs for other 20 seconds.

| Paclitaxel albumine - MDA-MB-231 | | | | | |
|---|---|---|---|---|---|
| Cell Death %<br>Total concentration<br>50 µM | Increasing %<br>vs NO-US | Cell Death %<br>Total concentration<br>10 µM | Increasing %<br>vs NO-US | Cell Death %<br>Total concentration<br>0.5 µM | Increasing %<br>vs NO-US |

| | | | | | | |
|---|---|---|---|---|---|---|
| NO - US | 17.8% | — | 9.4% | — | 5% | — |
| US - DC = 12% | 21.6% | +21.3% | 11.3% | +20.2% | 7.8% | +56% |
| US - DC = 9% | 45.1% | +153.4% | 31.9% | +239.4% | 80.9% | +282% |

Figure 3B:
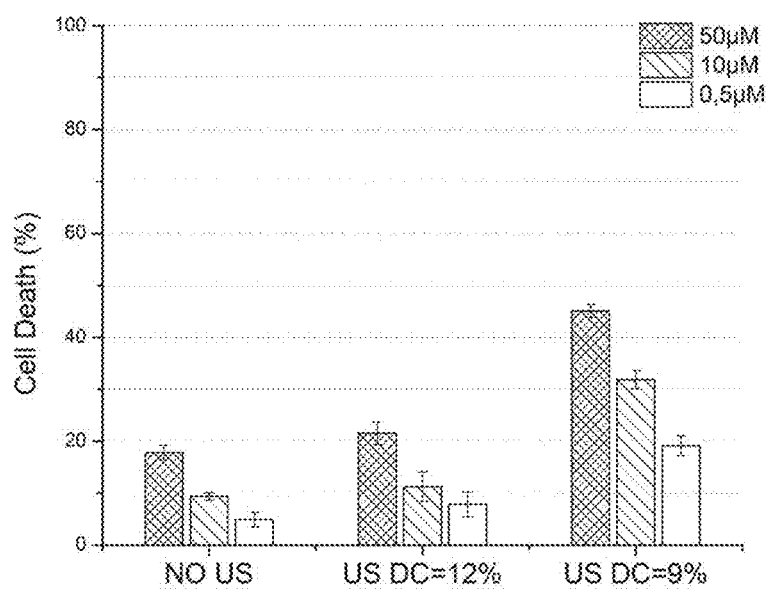
FIG. 3b shows the percentage of cell death obtained by in-vitro administering paclitaxel albumine to estrogen independent human breast adenocarcinoma cells, said administration being performed simultaneously to the administration of ultrasound waves. The figure shows the results obtained with different total concentrations (50 µM, 10 µM, 0.5 µM)

The results of the table above are graphically represented in FIG. 3b.

Example 7

In the following table the percentage of cell death are reported for three different concentration of doxorubicin administered to cells of MDA-MB-231 in three conditions:

NO-US: a first administration of a first dose of paclitaxel without administration of ultrasounds (NO-US) followed by a second administration of a second dose of doxorubicin;

US-DC=12%: first administration of a first dose of doxorubicin and simultaneous administration of pLINFUs (with duty cycle=12%) for 20 seconds followed by a second administration of a second dose of doxorubicin and simultaneous administration of pLINFUs for other 20 seconds;

US-DC=9%: first administration of a first dose of doxorubicin and simultaneous administration of pLINFUs (with duty cycle=9%) for 20 seconds followed by a second administration of a second dose of doxorubicin and simultaneous administration of pLINFUs for other 20 seconds.

| Doxorubicin - MDA-MB-231 | | | | | |
|---|---|---|---|---|---|
| Cell Death %<br>Total concentration<br>1000 µg/ml | Increasing %<br>vs NO-US | Cell Death %<br>Total concentration<br>500 µg/ml | Increasing %<br>vs NO-US | Cell Death %<br>Total concentration<br>100 µg/ml | Increasing %<br>vs NO-US |

| | | | | | | |
|---|---|---|---|---|---|---|
| NO - US | 54.5% | — | 22.8% | — | 10.9% | — |
| US - DC = 12% | 54.6% | +0.3% | 27% | +18.4% | 12% | +11.8% |
| US - DC = 9% | 60.5% | +11.1% | 38.8% | +70.5% | 23.5% | +116% |

Figure 4A:
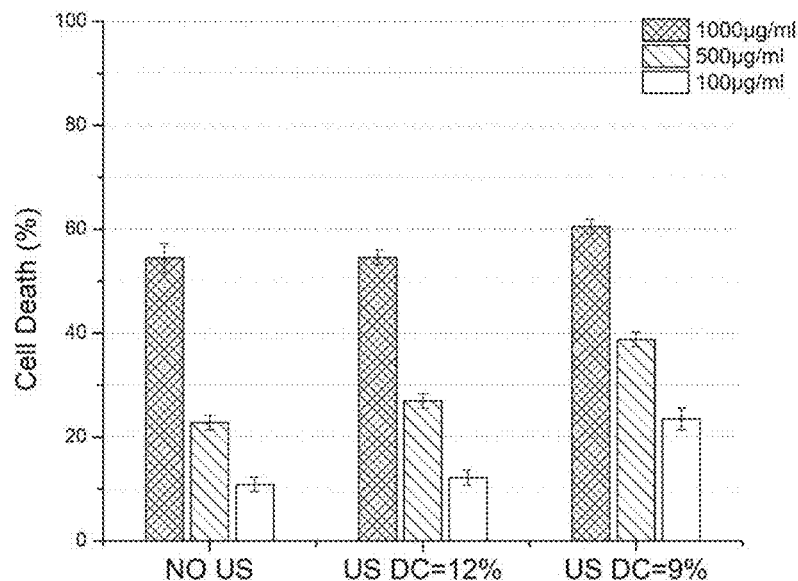
FIG. 4a shows the percentage of cell death obtained by in-vitro administering doxorubicin to estrogen independent human breast adenocarcinoma cells, said administration being performed simultaneously to the administration of ultrasound waves. The figure shows the results obtained with different total concentrations (1000 µg/ml, 500 µg/ml, 100 µg/ml)

The results of the table above are graphically represented in FIG. 4a.

Example 8

In the following table the percentage of cell death are reported for three different concentration of liposomal doxorubicin administered to cells of MDA-MB-231 in three conditions:

NO-US: a first administration of a first dose of paclitaxel without administration of ultrasounds (NO-US) followed by a second administration of a second dose of liposomal doxorubicin;

US-DC=12%: first administration of a first dose of liposomal doxorubicin and simultaneous administration of pLINFUs (with duty cycle=12%) for 20 seconds followed by a second administration of a second dose of liposomal doxorubicin and simultaneous administration of pLINFUs for other 20 seconds;

US-DC=9%: first administration of a first dose of liposomal doxorubicin and simultaneous administration of pLINFUs (with duty cycle=9%) for 20 seconds followed by a second administration of a second dose of liposomal doxorubicin and simultaneous administration of pLINFUs for other 20 seconds.

| Liposomal doxorubicin - MDA-Mb-231 | | | | | |
|---|---|---|---|---|---|
| Cell Death % Total concentration 1000 µg/ml | Increasing % vs NO-US | Cell Death % Total concentration 500 µg/ml | Increasing % vs NO-US | Cell Death % Total concentration 100 µg/ml | Increasing % vs NO-US |
| NO - US | 65.7% | — | 29% | — | 11.1% | — |
| US - DC = 12% | 72.4% | +10.2% | 37.8% | +30.4% | 17.1% | +53.9% |
| US - DC = 9% | 81.3% | +23.7% | 51.2% | +76.6% | 29.4% | +164.6% |

Figure 4B:
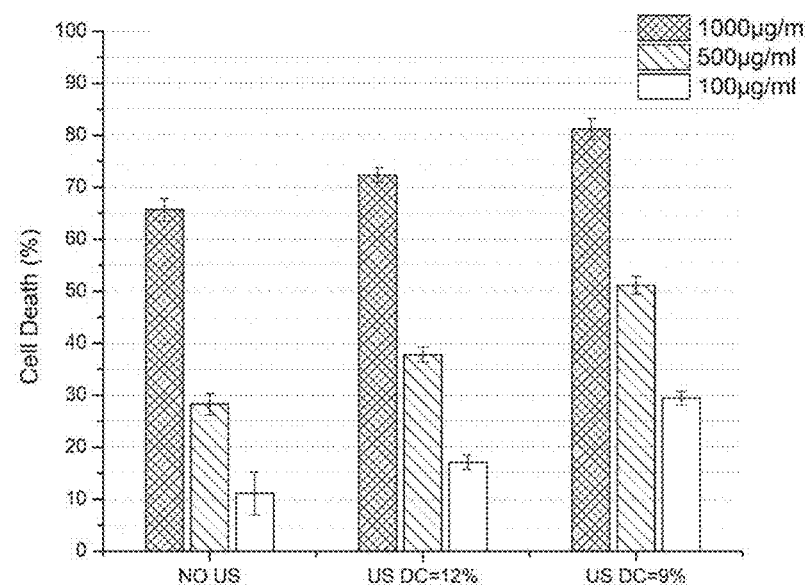
FIG. 4b shows the percentage of cell death obtained by in-vitro administering liposomal doxorubicin to estrogen independent human breast adenocarcinoma cells, said administration being performed simultaneously to the administration of ultrasound waves. The figure shows the results obtained with different total concentrations (1000 µg/ml, 500 µg/ml, 100 µg/ml)

The results of the table above are graphically represented in FIG. 4b.

Example 9

In the following table the percentage of cell death are reported for three different concentration of paclitaxel administered to cells of MiaPaCa2 in three conditions:

NO-US: a first administration of a first dose of paclitaxel without administration of ultrasounds (NO-US) followed by a second administration of a second dose of paclitaxel;

US-DC=12%: first administration of a first dose of paclitaxel and simultaneous administration of pLINFUs (with duty cycle=12%) for 20 seconds followed by a second administration of a second dose of paclitaxel and simultaneous administration of pLINFUs for other 20 seconds;

US-DC=1%: first administration of a first dose of paclitaxel and simultaneous administration of pLINFUs (with duty cycle=1%) for 20 seconds followed by a second administration of a second dose of paclitaxel and simultaneous administration of pLINFUs for other 20 seconds.

| Paclitaxel - MiaPaCa2 | | | | | |
|---|---|---|---|---|---|
| Cell Death % Total concentration 50 µM | Increasing % vs NO-US | Cell Death % Total concentration 10 µM | Increasing % vs NO-US | Cell Death % Total concentration 0.5 µM | Increasing % vs NO-US |
| NO - US | 80.2% | — | 65.3% | — | 45.5% | — |
| US - DC = 12% | 87.6% | +9.2% | 9.2% | +12.7% | 12.7% | 17.1% |
| US - DC = 1% | 90.5% | +12.8% | 12.8% | +22.7% | 22.7% | 40.1% |

Figure 5A:
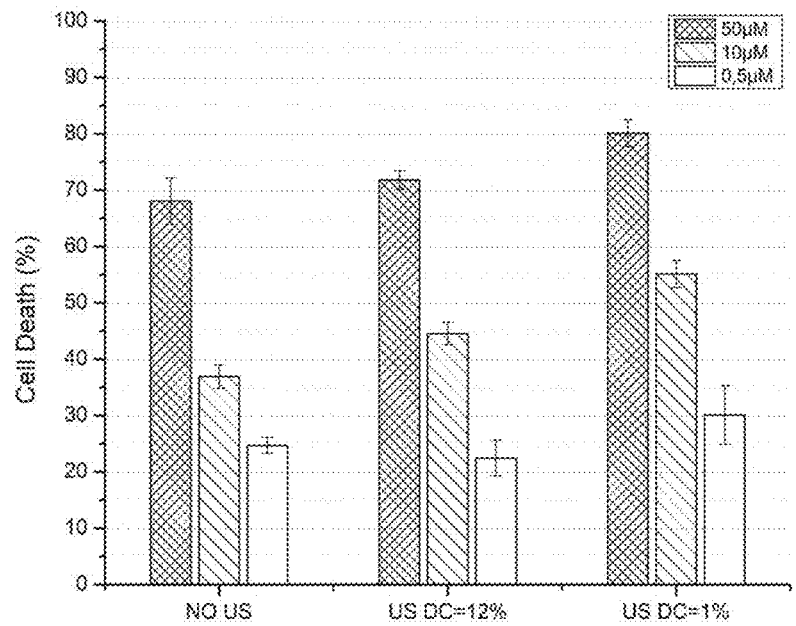
FIG. 5a shows the percentage of cell death obtained by in-vitro administering paclitaxel to estrogen independent human breast adenocarcinoma cells, said administration being performed simultaneously to the administration of ultrasound waves. The figure shows the results obtained with different total concentrations (50 µM, 10 µM, 0.5 µM)

The results of the table above are graphically represented in FIG. 5a.

Example 10

In the following table the percentage of cell death are reported for three different concentration of paclitaxel albumine administered to cells of MiaPaCa2 in three conditions:

NO-US: a first administration of a first dose of paclitaxel albumine without administration of ultrasounds (NO-US) followed by a second administration of a second dose of paclitaxel albumine;

US-DC=12%: first administration of a first dose of paclitaxel albumine and simultaneous administration of pLINFUs (with duty cycle=12%) for 20 seconds followed by a second administration of a second dose of paclitaxel albumine and simultaneous administration of pLINFUs for other 20 seconds;

US-DC=1%: first administration of a first dose of paclitaxel albumine and simultaneous administration of pLINFUs (with duty cycle=1%) for 20 seconds followed by a second administration of a second dose of paclitaxel albumine and simultaneous administration of pLINFUs for other 20 seconds.

| Paclitaxel albumine - MiaPaCa2 | | | | | |
|---|---|---|---|---|---|
| Cell Death % Total concentration 50 µM | Increasing % vs NO-US | Cell Death % Total concentration 10 µM | Increasing % vs NO-US | Cell Death % Total concentration 0.5 µM | Increasing % vs NO-US |
| NO - US | 7.9% | — | 6.4% | — | 6.4% | — |
| US - DC = 12% | 12.3% | +55.3% | 7.4% | +15% | 5.9% | −7.8% |
| US - DC = 1% | 25.5% | +221.9% | 14.7% | +128.4% | 11.3% | +76.6% |

Figure 5B:
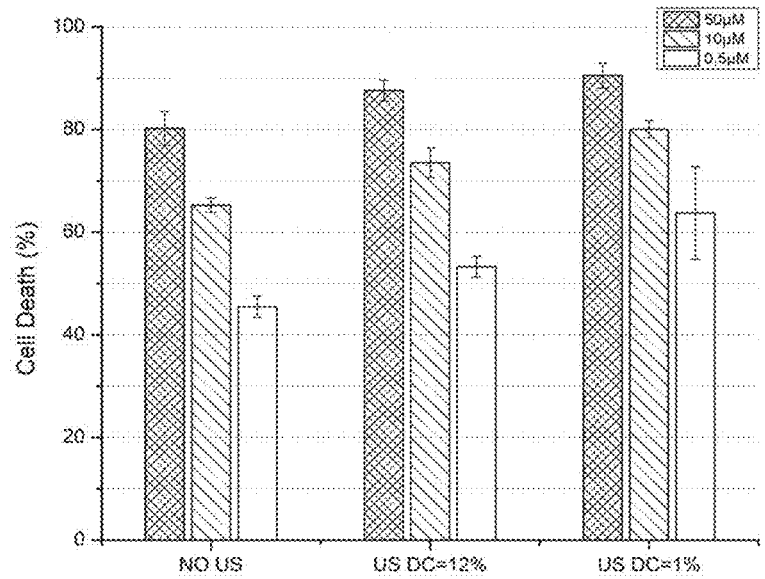
FIG. 5b shows the percentage of cell death obtained by in-vitro administering paclitaxel albumine to human pancreatic adenocarcinoma cells, said administration being performed simultaneously to the administration of ultrasound waves. The figure shows the results obtained with different total concentrations (50 µM, 10 µM, 0.5 µM)

The results of the table above are graphically represented in FIG. 5b.

Example 11

In the following table the percentage of cell death are reported for three different concentration of irinotecan administered to cells of MiaPaCa2 in three conditions:
- NO-US: a first administration of a first dose of irinotecan without administration of ultrasounds (NO-US) followed by a second administration of a second dose of irinotecan;
- US-DC=12%: first administration of a first dose of irinotecan and simultaneous administration of pLINFUs (with duty cycle=12%) for 20 seconds followed by a second administration of a second dose of irinotecan and simultaneous administration of pLINFUs for other 20 seconds;
- US-DC=1%: first administration of a first dose of irinotecan and simultaneous administration of pLINFUs (with duty cycle=1%) for 20 seconds followed by a second administration of a second dose of irinotecan and simultaneous administration of pLINFUs for other 20 seconds.

| Irinotecan - MiaPaCa2 | | | | | |
|---|---|---|---|---|---|
| Cell Death % Total concentration 50 µM | Increasing % vs NO-US | Cell Death % Total concentration 1 µM | Increasing % vs NO-US | Cell Death % Total concentration 0.05 µM | Increasing % vs NO-US |
| NO - US | 56.7% | — | 21.1% | — | 11.5% | — |
| US - DC = 12% | 66% | +16.5% | 30% | +42.5% | 18.5% | +60.6% |
| US - DC = 1% | 74.3% | +31.1% | 34.3% | +62.9% | 25.4% | +120.8% |

Figure 6A:
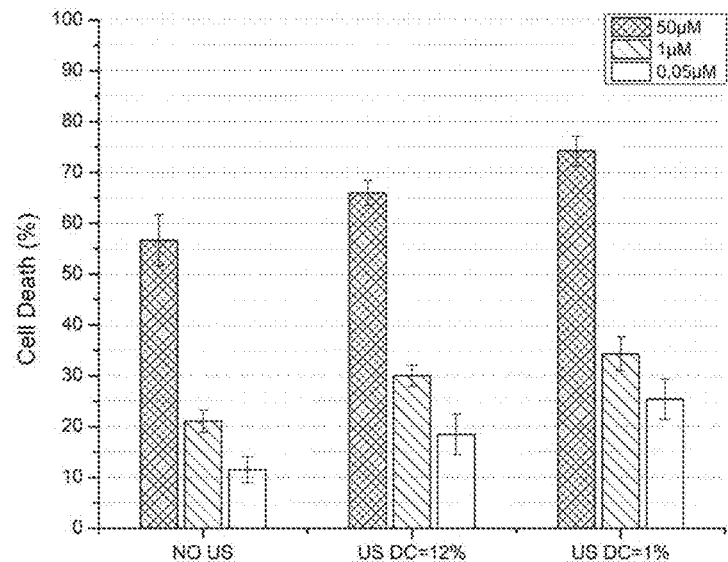
FIG. 6a shows the percentage of cell death obtained by in-vitro administering irinotecan to human pancreatic adenocarcinoma cells, said administration being performed simultaneously to the administration of ultrasound waves. The figure shows the results obtained with different total concentrations (50 µM, 10 µM, 0.05 µM)

The results of the table above are graphically represented in FIG. 6a.

Example 12

In the following table the percentage of cell death are reported for three different concentration of liposomal irinotecan and fluorouracil (FU) administered to cells of MiaPaCa2 in three conditions:
- NO-US: a first administration of a first dose of a solution containing liposomal irinotecan and fluorouracil, without administration of ultrasounds (NO-US) followed by a second administration of a second dose a solution containing liposomal irinotecan and fluorouracil;
- US-DC=12%: first administration of a first dose of a solution containing liposomal irinotecan and fluorouracil, and simultaneous administration of pLINFUs (with duty cycle=12%) for 20 seconds followed by a second administration of a second dose of a solution containing liposomal irinotecan and fluorouracil, and simultaneous administration of pLINFUs for other 20 seconds;
- US-DC=1%: first administration of a first dose of a solution containing liposomal irinotecan and fluorouracil, and simultaneous administration of pLINFUs (with duty cycle=1%) for 20 seconds followed by a second administration of a second dose of a solution containing liposomal irinotecan and fluorouracil, and simultaneous administration of pLINFUs for other 20 seconds.

| Liposomal irinotecan + Fluorouracil (FU) - MiaPaCa2 | | | | | |
| --- | --- | --- | --- | --- | --- |
| Cell Death % Total concentration 50 µM + 5 FU 100 µM | Increasing % vs NO-US | Cell Death % Total concentration 1 µM + 5 FU 10 µM | Increasing % vs NO-US | Cell Death % Total concentration 0.05 µM + 5 FU 1 µM | Increasing % vs NO-US |
| NO - US            85% | — | 67% | — | 25% | — |
| US - DC = 12%   89% | +4.7% | 80.5% | +20.1% | 39% | +56% |
| US - DC = 1%    98% | +11.8% | 88% | +31.3% | 53.5% | +114% |

Figure 6B:
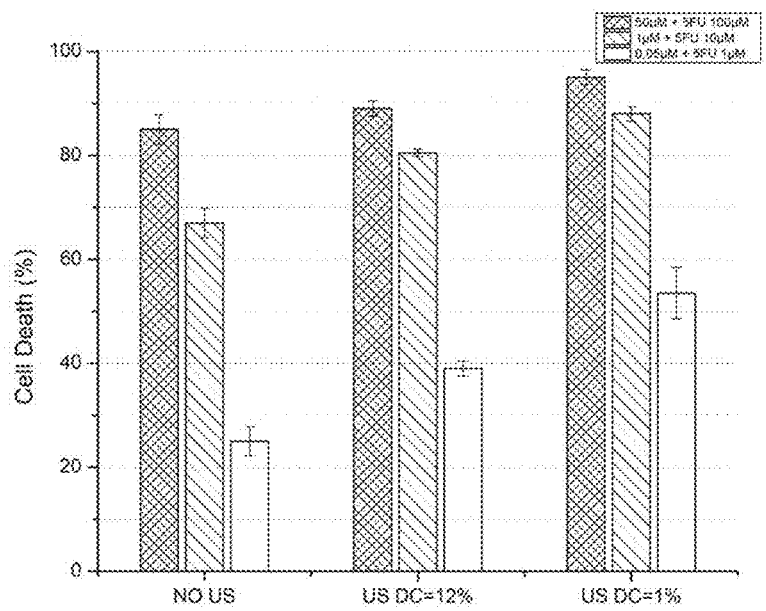
FIG. 6b shows the percentage of cell death obtained by in-vitro administering liposomal irinotecan together with fluorouracil to human pancreatic adenocarcinoma cells, said administration being performed simultaneously to the administration of ultrasound waves. The figure shows the results obtained with different total concentrations (50 µM, 10 µM, 0.05 µM)

The results of the table above are graphically represented in FIG. 6b.

Example 13

Figure 7:
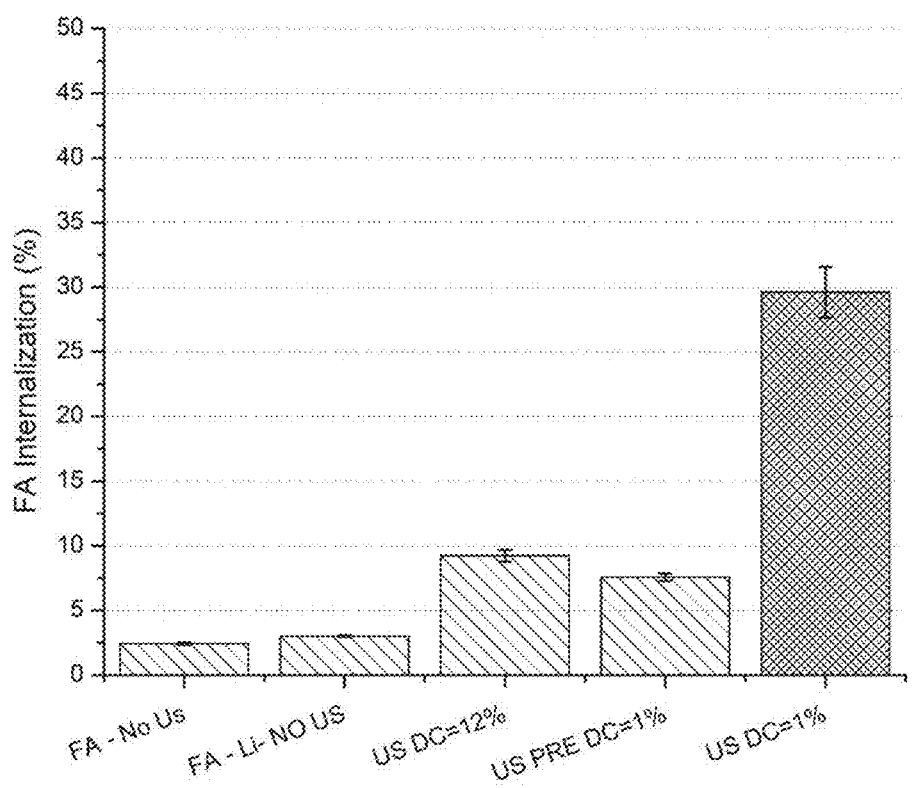
FIG. 7 shows the results relative to an experiment of internalization of a fluoresceinamine (FA) in cancer cells.

This example is relative to an experiment of internalization of a fluoresceinamine (FA). FIG. 7 shows in particular the uptake of FA into human pancreatic adenocarcinoma cells in five experimental conditions, said conditions being specifically designed in order to compare the effect of the administration of ultrasounds. The tested experimental condition are:

FA-NO-US-NO DRUG: administration of FA alone, without administration of any drug and without administration of ultrasounds;

FA-LI-NO-US: administration of FA and liposomal irinotecan (LI), without administration of ultrasounds;

US-DC=12%: administration of FA and liposomal irinotecan (LI), with the simultaneous administration of pLINFUs with a duty cycle of 12%;

US-PRE-DC=1%: administration of pLINFUs with a duty cycle of 1% followed by subsequent administration of FA and liposomal irinotecan (LI); and US-DC=1%: administration of FA and liposomal irinotecan (LI), with the simultaneous administration of pLINFUs with a duty cycle of 1%.

Figure 8A:
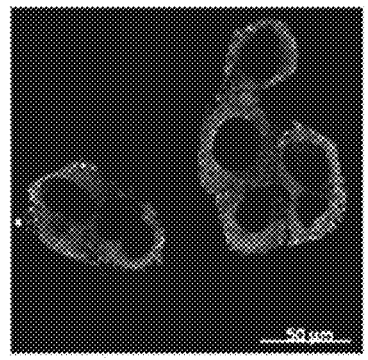
FIG. 8a shows an image obtained by Confocal Laser Scanning Microscopy (CLSM) of the intake of the FA into human pancreatic adenocarcinoma cells, said FA being administered alone, i.e. without administration of ultrasound and of any drug.
Figure 8B:
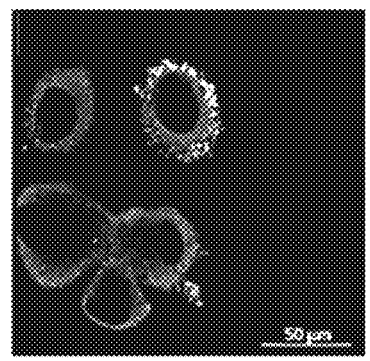
FIG. 8b shows an image obtained by Confocal Laser Scanning Microscopy (CLSM) of the intake of the FA into human pancreatic adenocarcinoma cells, said FA being administered together with liposomal irinotecan without administration of ultrasounds.
Figure 8C:
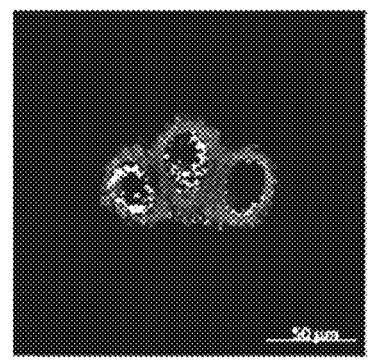
FIG. 8c shows an image obtained by Confocal Laser Scanning Microscopy (CLSM) of the intake of the FA into human pancreatic adenocarcinoma cells, said FA being administered together with liposomal irinotecan and simultaneously with the administration of pulsed ultrasounds with a duty cycle of 12%.
Figure 8D:
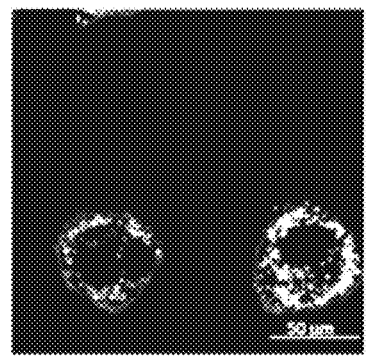
FIG. 8d shows an image obtained by Confocal Laser Scanning Microscopy (CLSM) of the intake of the FA into human pancreatic adenocarcinoma cells, said FA being administered together with liposomal irinotecan after the administration of pulsed ultrasounds with a duty cycle of 1%.
Figure 8E:
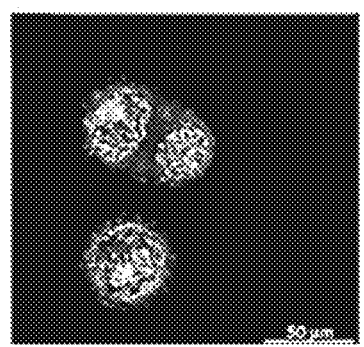
FIG. 8e shows an image obtained by Confocal Laser Scanning Microscopy (CLSM) of the intake of the FA into human pancreatic adenocarcinoma cells, said FA being administered together with liposomal irinotecan and simultaneously with the administration of pulsed ultrasounds with a duty cycle of 1%.
Figure 9A:
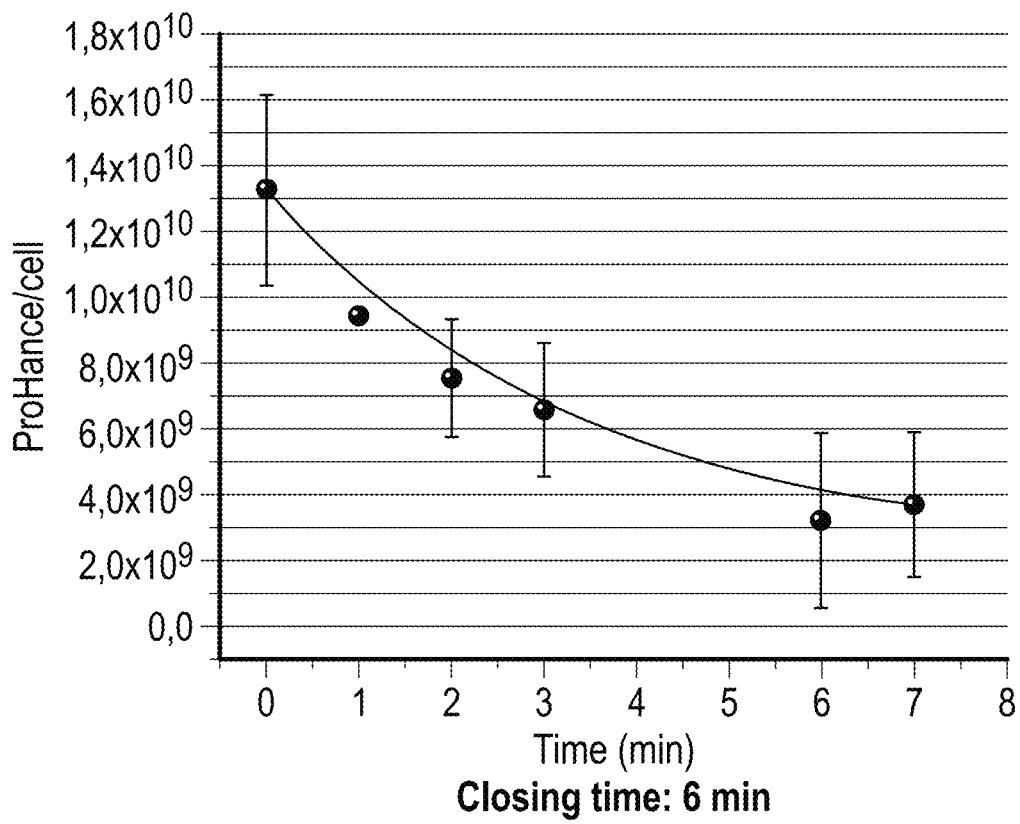
FIG. 9a shows the kinetics of cellular membrane pore's closure with Prohance (Gd3+)
Figure 9B:
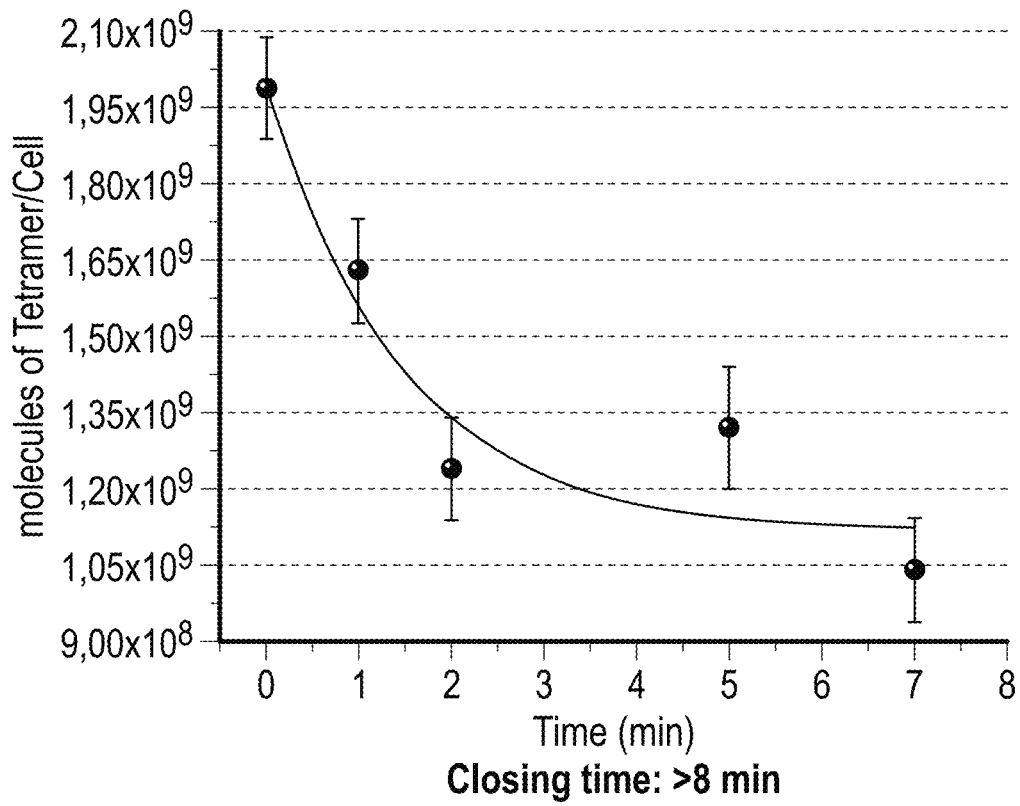
FIG. 9b shows the kinetics of cellular membrane pore's closure with Prohance and liposomes.
Figure 9C:
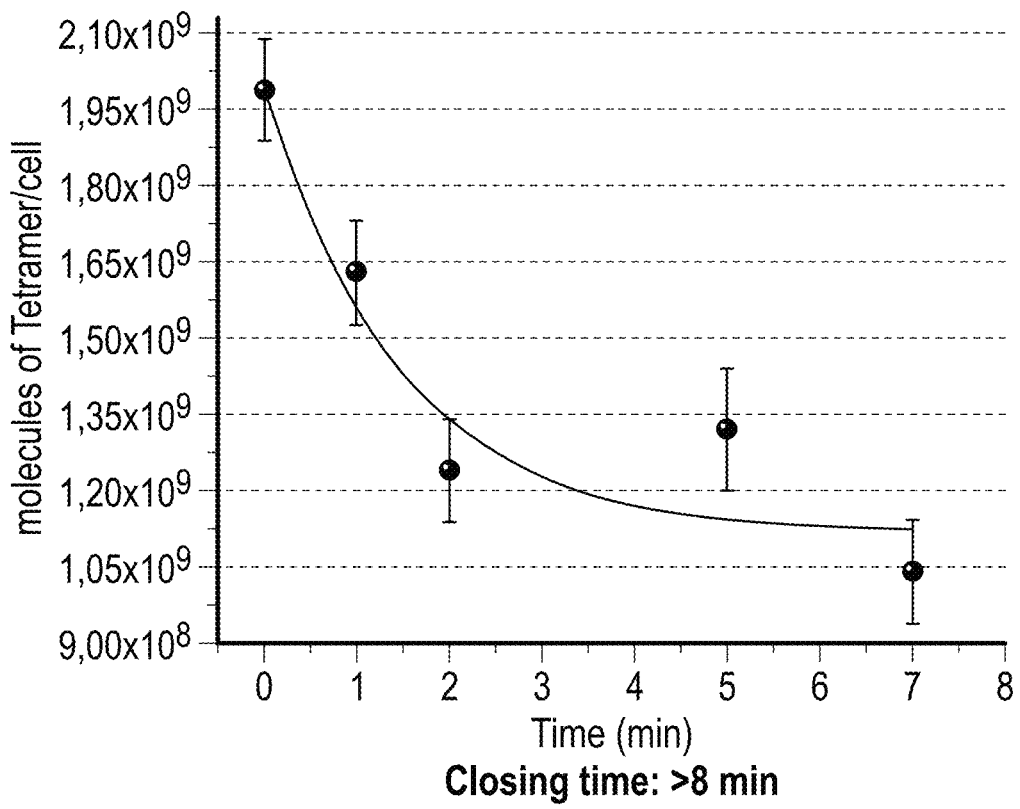
FIG. 9c shows the kinetics of cellular membrane pore's closure with Tetramer.
Figure 9D:
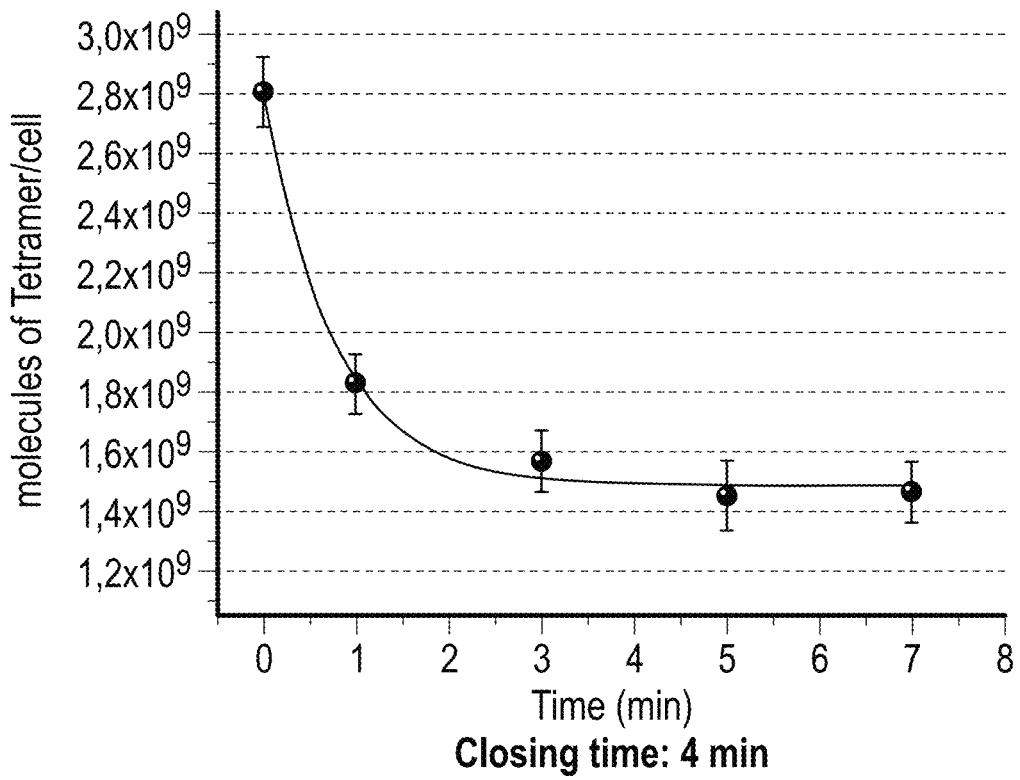
FIG. 9d shows the kinetics of cellular membrane pore's closure with Tetramer and liposomes.

In FIG. 7, it is graphically represented the FA Internalization (%), i.e. the percentage of FA measured after the removal of the surfactant liquid from the cell culture wells, i.e. the percentage of FA inside the cell. The results of the experiment of this example were also analyzed by Confocal Laser Scanning Microscopy (CLSM) after 2 hours of incubation. FIGS. 8a, 8b, 8c, 8d, 8e show the intake of the FA into human pancreatic adenocarcinoma cells, in the five aforementioned experimental conditions. From FIG. 7, it can be deducted that the higher FA internalization % is obtained with the condition US-DC=1%. From these images it is possible to see how FA alone (represented in white) is not accumulated in the cells (represented in grey) (FIG. 8a).

When FA is administered together with liposomal irinotecan (FIG. 8b) a greater fluorescence density is observed, but only at an extracellular perimembrane level. It can be explained with a greater chemical interaction between the polymeric chains of polyethylene glycol of the liposomal membrane and the FA. In the FIG. 8c and FIG. 8d (US-DC=12% and US-PRE-DC=1%, respectively), the presence of FA inside the cells became evident and the highest level of FA internalization is showed in FIG. 8e corresponding to the US-DC=1% condition. In the condition US-PRE-DC=1% a certain grade of FA internalization is achieved, probably, due to the fact that after administration of ultrasounds, the cells membranes need some tens of seconds to return to the permeability that they have before sonoporation.

Example 14

This example is relative to the study of the opening and the closing of pores in breast cancer cells. For each point of the graph (FIG. 9a, 9b, 9c, 9d) a sample is sonoporated. All the samples contains the same amount of cells. On the X axis are reported the times between the end of the cell sonoporation and the addition of the substance whose internalization must be measured in the cells. The experiment of internalization is the following:

Time 0 min: as soon as 1 minute of sonoporation has been completed, a fixed amount of Prohance (contrast medium for magnetic resonance) is added to the cell culture; after 1 minute the cells are isolated.

Time 1 min: 1 minute of sonoporation, then after 1 minute a fixed amount of Prohance is added to the cell culture, after another minute the cells are isolated Time n min: 1 minute of sonoporation, then after n minutes a fixed amount of Prohance is added to the cell culture; after another minute the cells are isolated.

These tests, in addition to those performed on other types of cells, have shown that the closing time of cell pores depends on:

type of cells;

type of drug molecule (Prohance and Tetramer simulated the presence of pharmacological molecules of different composition and size)

presence or absence of vector agents (liposomes)

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited.

Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus the scope of the invention should be determined by the appended claims and their legal equivalents, and not by the examples given.

The claims in the instant application are different than those of the parent application or other related applications. Applicant therefore rescinds any disclaimer of claim scope made in the parent application or any predecessor application in relation to the instant application. Any such previous disclaimer and the cited references that it was made to avoid, may need to be revisited. Further, any disclaimer made in the instant application should not be read into or against the parent application.

The invention claimed is:

1. A method for controlling ultrasonic waves to induced sonoporation of a drug into cancer cells in a tumor, the method comprising:
   accessing configuration data that includes a type of the tumor and a type of drug;
   determining values of operational parameters based on the configuration data to define determined values, the operational parameters including frequency value and duty cycle value;
   determining frequency value based on the type of tumor to define a determined frequency value;
   determining the duty cycle value based on the type of drug and the type of tumor to define a determined duty cycle value; and
   controlling a generator and at least one ultrasound probe to operate according to the determined frequency value and the determined duty cycle value.

2. The method according to claim 1, further comprising automatically tuning the determined frequency value and an amplitude of the ultrasonic waves to compensate for attenuation of the ultrasonic waves caused by a medium interposed between the at least one ultrasound probe used to emit the ultrasonic waves and the cancer cells.

3. The method according to claim 2, wherein the determined frequency value and the amplitude of the ultrasonic waves are automatically tuned synchronously with the duty cycle value.

4. The method according to claim 3, wherein the at least one ultrasound probe comprises a plurality of ultrasound transducers comprising a first subset of ultrasound transducers and a second subset of ultrasound transducers; wherein the first subset of ultrasound transducers are configured as ultrasound emitters for converting electrical energy into the ultrasonic waves for inducing sonoporation; and wherein the second subset of ultrasound transducers are configured as ultrasound receivers for converting ultrasonic waves reflected by the medium interposed into an electric signal readable by a processor; and wherein the method further comprises:
   calculating a difference of frequency and amplitude between the ultrasonic waves emitted by the first subset of transducers and the ultrasonic waves received by the second subset of transducers to define calculated differences; and
   adjusting the amplitude and the frequency of the ultrasonic waves to compensate for the calculated differences.

5. The method according to any claim 3, wherein the at least one ultrasound probe comprises an ultrasound transducer; wherein the ultrasound transducer is configured as an ultrasound emitter for converting electrical energy into the ultrasonic waves for inducing sonoporation; and wherein the ultrasound transducer is further configured as an ultrasound receiver to convert the ultrasonic waves reflected by the medium interposed into an electric signal readable by a processor; and wherein the method further comprises:
   calculating a difference of frequency and amplitude between the ultrasonic waves emitted and the ultrasonic waves received by the ultrasound transducer to define a calculated difference; and
   adjusting the amplitude and the frequency of the ultrasonic waves to compensate for the calculated difference.

6. The method according to claim 1, further comprising storing a list of values of frequency and a list of values of duty cycle on a computer readable memory; assigning a value of frequency to a type of tumor; defining a coupled configuration data that includes a type of tumor and a type of drug; and assigning a value of duty cycle to the coupled configuration data.

7. The method according to claim 1, wherein the tumor is selected from the group consisting of human breast ductal carcinoma, estrogen independent human breast adenocarcinoma, human pancreatic adenocarcinoma, human melanoma, human lentiginous melanoma, human lentigo maligna melanoma, human superficial spreading melanoma, human acral lentiginous melanoma, human mucosal melanoma, human nodular melanoma, human polypoid melanoma, human small cell melanoma, human Spitzoid melanoma, human uveal melanoma and human desmoplastic melanoma, hepatocellular carcinoma.

8. The method according to claim 2, wherein the configuration data includes anthropometric measurements being selected from a group consisting of abdominal circumference, body mass index, breast circumference, thorax circumference, and body fat percentage.

9. The method according to claim 8, wherein the frequency value of the operational parameter is determinable based on the anthropometric measurements.

10. The method according to claim 9, further comprising defining a set of coupled configuration data that includes a type of tumor and at least one anthropometric measurement; and assigning a value of the frequency to the set of coupled configuration data.

11. The method according to claim 1, wherein the configuration data includes a grade of the tumor; and wherein the grade of the tumor comprises at least one of primary tumor, primitive tumor, and secondary tumor, and metastasis.

12. The method according to claim 2, wherein the configuration data includes a localization of a secondary tumor.

13. The method according to claim 12, wherein the duty cycle value is determinable based on the localization of the secondary tumor.

14. The method according to claim 12, defining a set of coupled configuration data that includes the type of tumor, the type of drug, the grade of the tumor, and the localization of the secondary tumor; and assigning a value of the duty cycle to the set of coupled configuration data.

15. The method according to claim 1, wherein the type of drug comprises at least one of paclitaxel, paclitaxel albumine, doxorubicin, liposomal doxorubicin, irinotecan, liposomal irinotecan and fluorouracil.

16. The method according to claim 1, wherein the operational parameters comprise an operation time of the ultrasonic waves; wherein a value of the operation time is determinable based on at least one of the type of tumor and the type of drug; and wherein the method further comprises defining a coupled configuration data that includes the type of tumor and the type of drug; and assigning the value of the operation time to the coupled configuration data.

17. The method according to claim 16, wherein the operation time comprises at least one of:
 a single temporal window in which ultrasonic waves are administered; and
 at least two temporal windows in which during a first one of the at least two temporal windows, ultrasonic waves are administered, and during a second one of the at least two temporal windows, no ultrasonic waves are administered, so that ultrasonic waves are administered in alternating temporal windows and separated by a single temporal window where no ultrasonic waves are administered.

18. The method according to claim 1, wherein the determined frequency value is between 0.6 MHz and 3 MHz; wherein the determined duty cycle value is below 12%.

19. A computer program product comprising code to control ultrasonic waves to induced sonoporation of a drug into cancer cells in a tumor, the computer program product being operable to:
 access configuration data that includes a type of the tumor and a type of the drug;
 determine values of operational parameters based on the configuration data to define determined values, the operational parameters including frequency value and duty cycle value;
 determine frequency value based on the type of tumor to define a determined frequency value;
 determine the duty cycle value based on the type of drug and the type of tumor to define a determined duty cycle value; and
 controlling a generator and at least one ultrasound probe to operate according to the determined frequency value and the determined duty cycle value.

20. A computer readable medium to store a computer program code to control ultrasonic waves to induced sonoporation of a drug into cancer cells in a tumor, the computer program product being executable to:
 access configuration data that includes a type of the tumor and a type of the drug;
 determine values of operational parameters based on the configuration data to define determined values, the operational parameters including frequency value and duty cycle value;
 determine frequency value based on the type of tumor to define a determined frequency value; and
 determine the duty cycle value based on the type of drug and the type of tumor to define a determined duty cycle value; and
 controlling a generator and at least one ultrasound probe to operate according to the determined frequency value and the determined duty cycle value.

* * * * *